US005868943A

United States Patent [19]

Donnelly, Jr.

[11] Patent Number: 5,868,943

[45] Date of Patent: Feb. 9, 1999

[54] WASTE TREATMENT PROCESS FOR THE DISPOSAL OF DICHLORODIFLUOROMETHANE BY CONVERSION INTO POLYTETRAFLUOROETHYLENE

[76] Inventor: Joseph L. Donnelly, Jr., 1463 La Salle, Burton, Mich. 48509-2407

[21] Appl. No.: 232,763

[22] Filed: Apr. 25, 1994

[51] Int. Cl.$^6$ .............................. C02F 1/00; C07C 17/00; C25B 3/10

[52] U.S. Cl. .......................... 210/753; 205/588; 210/749; 210/754; 210/805; 210/806; 570/157

[58] Field of Search .................................... 210/259, 638, 210/634, 749, 805, 753, 806, 754, 767; 570/156, 157; 205/406, 407, 408, 411, 558

[56] References Cited

U.S. PATENT DOCUMENTS

| | | | |
|---|---|---|---|
| 518,135 | 4/1894 | Castner . | |
| 578,457 | 3/1897 | Kellner . | |
| 1,613,966 | 1/1927 | Sorensen . | |
| 2,230,654 | 4/1941 | Plunkett | 260/94 |
| 2,393,967 | 2/1946 | Brubaker | 260/80 |
| 2,394,243 | 2/1946 | Joyce | 260/80 |
| 4,166,780 | 9/1979 | Bianchi et al. | 204/99 |

FOREIGN PATENT DOCUMENTS

| | | |
|---|---|---|
| 751481 | 4/1970 | Belgium . |

*Primary Examiner*—John Kim

[57] ABSTRACT

A saturated solution of an alkaline earth or alkali metal halide salt is electrolyzed in a flowing mercury cathode electrolysis cell. The amalgam is added dropwise to a solution of dichlorodifluoromethane in a solution of a polar, aprotic solvent, not reducible by such amalgams. The solvent contains inhibitors of polymerization, and may contain a promoting salt of lithium or the "onium" type. Tetrafluoroethylene and unreacted dichlorodifluoromethane gases are evolved, and separated by condensing the dichlorodifluoromethane. The polar, aprotic solvent is removed from the reaction and evaporated, crystallizing the chloride salt of the alkaline earth or alkali metal. This salt is combined with the anolyte of the mercury cell to form brine. The spent mercury from the dechlorination and dimerization is also recycled to the mercury cell. The polar, aprotic solvent is condensed, and mixed with the condensed unreacted dichlorodifluoromethane for further dechlorination and dimerization. The tetrafluoroethylene gas is polymerized in aqueous media, under heat and pressure to form polytetrafluoroethylene.

4 Claims, 1 Drawing Sheet

WASTE TREATMENT PROCESS FOR THE DISPOSAL OF DICHLORODIFLUOROMETHANE BY CONVERSION INTO POLYTETRAFLUOROETHYLENE

BACKGROUND-FIELD OF INVENTION

This invention relates to a waste treatment process, specifically to a superior waste disposal method for conversion of dichlorodifluoromethane into polytetrafluoroethylene.

BACKGROUND-DESCRIPTION OF PRIOR ART

Originally, dichlorodifluoromethane was developed for use as a refrigerant. Its use became worldwide, due to its many advantages over alternative refrigerants. Other uses for dichlorodifluoromethane have been developed, including those such as solvents, propellants, and foaming agents for plastics.

In 1974, dichlorodifluoromethane, because of its great chemical stability, was discovered by Rowland and Molina to be able to remain unchanged until reaching the stratosphere, where ultraviolet radiation was able to convert it into molecular chlorine, able to catalytically decompose ozone. The production and use of dichlorodifluoromethane has been controlled by the Montreal Protocol of the Vienna Convention, and the Stratospheric Ozone Protection Act. At present, recycling is mandated, however, since normal leakage is primarily responsible for remaining dichlorodifluoromethane emissions, many scientists worldwide are attempting to develop an economical waste disposal process.

Presently, incineration is the only known method for disposal of dichlorodifluoromethane, disadvantaged by its great expense. The present invention combines known prior technology to form a waste treatment process converting dichlorodifluoromethane into polytetrafluoroethylene. Mercury cathode electrolytic cells have been known since 1882. The dechlorination and dimerization of dichlorodifluoromethane has been known since 1969. The polymerization of tetrafluoroethylene into polytetrafluoroethlyene has been known since 1939. Evaporation and distillation of liquids, crystallization of chloride salts, and condensation of gases have all been known for hundreds or thousands of years. Until the present invention, these distinct processes have never been combined together. The present invention is the first commercially profitable method for the disposal of dichlorodifluoromethane. Obviously, the conversion of an environmentally dangerous waste product into a commercially salable product has been and is a primary goal of many research scientists around the world.

Objects and Advantages

It is an object of this invention to economically dispose of dichlorodifluoromethane, in consideration of reducing the damage to the stratospheric ozone layer. The known process of incineration is expensive and produces no commercially salable products.

It is a further object of this invention to use each product of the various reactions involved in an economical manner by recycling each as much as possible. The environmental impact of the disposal of dichlorofluoromethane must be minimized.

It is a further object of this invention to create a valuable commercial product from a waste material, thus accelerating the disposal of dichlorodifluoromethane.

BRIEF DESCRIPTION OF THE FIGURE

In the drawing, FIG. 1 comprises the entire process of converting dichlorodifluoromethane into polytetrafluoroethylene.

A is the brine saturation stage.

Figure 1:
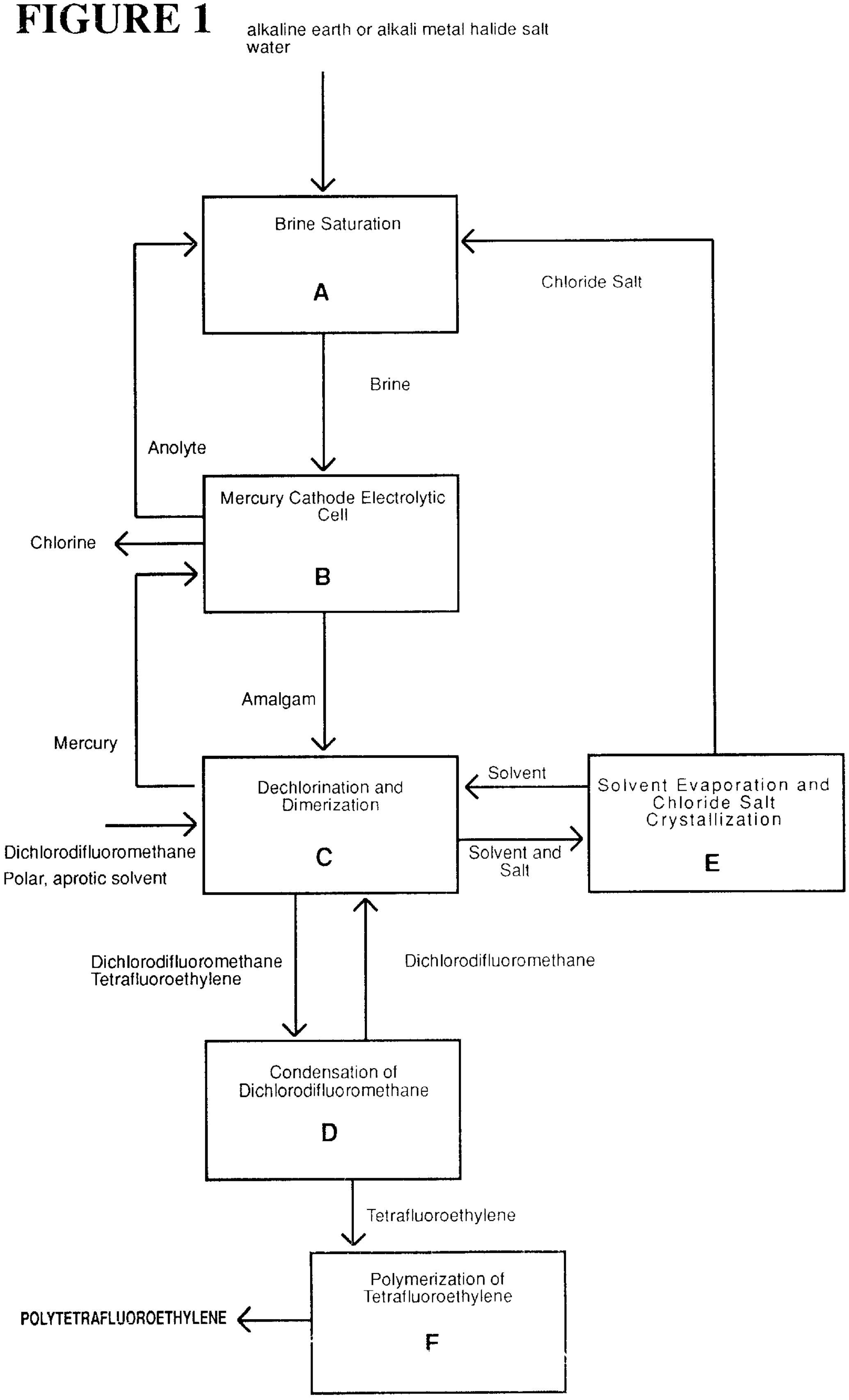

B is the mercury cathode electrolytic cell.

C is the dechlorination and dimerization reaction.

D is the condensation of dichlorodifluoromethane, for recycling in the dechlorination and dimerization reaction.

E is the removal of the polar, aprotic solvent from the dechlorination and dimerization reactor, for evaporation of the solvent and crystallization of the alkaline earth of alkali metal chloride salt for recycling to the brine saturation.

F is the polymerization of tetrafluoroethylene into polytetrafluoroethylene.

DESCRIPTION

Mercury cathode electrolytic cells can be any shape capable of containing the reaction, and are constructed of any suitable material, such as concrete. The cathode is flowing mercury, which can be horizontal or vertical. The insoluble anode may be of any material capable of serving that purpose, but typically is constructed of platinum-coated titanium or graphite. Usually, a horizontal flowing mercury cathode is used, with an inclined steel trough, approximately 0.5° to 1.5°. The cell cover may be constructed of any material resistant to chlorine. The sides of the cell are usually lined with rubber. The cell cover may be constructed of any material resistant to chlorine. The brine saturator may be of any vessel that can hold brine. Gravity or pumps transfer the amalgam to the dechlorination and dimerization reactor. The reactor may be of any configuration and material, though usually it would be cylindrical and constructed of glass-lined steel. The amalgam is admitted into the reactor through one or many dropping units. The reactor ordinarily would have internal cooling units, and agitators. A condenser of any material, but normally metallic, tops the dechlorination and dimerization reactor. The evaporator can be either a noncirculating or a circulating evaporator, made of any material. The solvent condenser could be made from any material, but is usually metallic. Pumps are used for transfers of liquids, or gravity. The polymerization reactor may be of any material and construction that can withstand the pressure used.

Operation

The brine is prepared by saturating water with an alkaline earth or alkali metal halide salt. The brine is fed into the mercury cell by a pump or by gravity. The electrolytic cell uses a flowing mercury cathode, in which the alkaline earth or alkali metal is deposited into the flowing mercury cathode, forming an amalgam. Typically, direct current energy is applied to the electolytic cell at a voltage in the range of 4 to 4.5 volts. The brine and mercury flow concurrently. Chlorine gas is also generated by the decomposition reaction. The amalgam is admitted dropwise into the dechlorination and dimerization reactor, which contains dichlorodifluoromethane dissolved in a polar, aprotic solvent resistant to the reducing action of an alkaline earth or alkali metal amalgam. These solvents can be compounds of, or mixtures of the hydrocarbons, the acyclic amides, the saturated nitriles, the simple or substituted lactams, the sulfones, the sulfoxides, the ethers, the phosphoric esters, or the alkyl carbonates. Specific examples of solvents are benzene, toluene, isooctane, n-octane, n-heptane, petroleum ether, hexane, cyclohexane, N-dimethylformamide, N-methylacetamide, hexamethylphosphorictriamide, and analogues; pyrrolidones, N-methylpyrrolidone, ethylene, bis-pyrrolidone, valeric lactam, caproic lactam, ethyl caproic lactam and analogues; acetonitrile, propionitrile, benzonitrile and analogues; dimethylsuloxide, sulfolane, sulfonal, diphenylsulfoxide, diphenylsulfone and analogues; methylethyl ether, diethyl ether, methyl n-propyl ether, methylisopropyl ether, trimethylene glycol, dimethyl ether, dioxane, monomethyl ether acetate of ethylene glycol, tetrahydrofuran and analogues; diethyl carbonate, propylene carbonate, and analogues; and trimethylphosphate, triethyl phosphate, tri-n-butyl phosphate, or methyldiethylphosphate. The polar, aprotic solvent contains a polymerization inhibitor such as the phenols, the terpenes, or the quinones. The polar, aprotic solvent may contain a promoter in variable quantities from 0.001 to 20 parts by weight to 100 parts of solvent. Any "onium" salt or salt of lithium chloride may serve as a promoter. The salts of the "onium" type are salts of the following formulas:

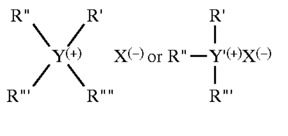

in which Y is nitrogen or phosphorus, and Y' is oxygen or sulfur, and R', R", R'", and R"" can be the same or different, and can represent alkyl, aryl, alkylaryl, arylalkyl, and cycloalkyl radicals containing one or more heteroatoms like nitrogen, oxygen, and sulfur, X is a halogen anion, either fluoride, chloride, bromide or iodide, or a sulfate group, a cyanosulfide, a cyanooxide, the anion of organic sulfonic acid, or the anion of a carboxylic acid, or any anion analogue of acids nonreducible by alkaline earth or alkali metal amalgams.

Specific examples are tetramethylammonium paratoluenesulphonate, methyltributylammonium paratoluenesulfonate, triethylmethylammonium paratoluenesulfonate, tetramethylketylammonium bromide, trimethylcyclopentylammonium bromide, trimethylethylammonium chloride, distearyldimethylammonium chloride, trimethyl para-tolylammonium iodide, N-dimethylmorpholine iodide, alpha- or beta- napthalene tetramethyl ammonium sulfonate, benzyltriethylammonium phosphate, benzyltrimethylammonium thiocyanate, N-methyl-N-ethylpiperidinoiodide, tetrabutyl ammonium fluoride, trimethylcyclohexyl ammonium acetate, and tetramethyl phosphonium iodide. The temperature that the dechlorination and dimerization is carried out at can vary between −40° C. and 110° C. The pressure can vary between atmospheric and 40 atmospheres. The alkaline earth or alkali metal amalgam concentration varies between 0.01 and 1%, by weight. The process may be run batchwise or continuously. The reaction is exothermic, regulated by the amount of amalgam, or external cooling such as coils or a thermostatic bath. Tetrafluoroethylene and unreacted dichlorodifluoromethane gases are evolved. These gases are seperated by a condenser or column atop the dimerization and dechlorination reactor. The dichlorodifluoromethane is recycled into the polar, aprotic solvent. The tetrafluoroethylene is polymerized in the conventional manner, under heat and pressure, in the presence of water, and an organic peroxy compound such as ammonium peroxydisulfate. A dispersing agent, such as a perfluoro-alkanoic acid salt, for example ammonium perfluorooctanoate may be used. A typical temperature for polymerization would be 60° C., and a pressure up to 1000 atmospheres. A pure hydrocarbon wax may be mixed in with the aqueous solution. The tetrafluoroethylene may also be copolymerized with other alkenes, such as ethylene or propylene. The polar, aprotic solvent is withdrawn as the dechlorination and dimerization reaction ends if it is being run batchwise, or continuously otherwise. The solvent is evaporated, with the alkaline earth or alkali metal chloride salt produced being crystallized. The polar, aprotic solvent is recycled with the unreacted dichlorodifluoromethane to the dechlorination and dimerization reaction. The crytallized salt is recycled to the brine saturation stage. The spent mercury is withdrawn from the dechlorination and dimerization reaction and transferred by a pump, or other means, back to the mercury cathode electrolysis cell. The anolyte is recycled.

Working Example of Process 21.93 g of NaCl is dissolved in 627 ml of water. The solution is electrolyzed at 4.5 V and 2.5 A, with vigorous stirring, in a bench scale mercury cathode cell, until the sodium concentration is 0.25%, the cell containing 424 g of Hg. The resulting sodium amalgam is mixed with 549.9 g of Hg. The diluted sodium amalgam is admitted dropwise for 107.5 minutes into a vigorously stirred solution of 7.25 g dichlorodifluoromethane and 0.75 g of tetraethylammonium paratoluene sulfonate dissolved 96 g of N,N-dimethylformamide. During the course of the reaction, the temperature was maintained at 20° C. with 6 g of ice. The product gas, which forms very quickly, is passed through a condenser cooled to −52° C. by ethyl alcohol mixed with dry ice. The resulting tetrafluoroethylene gas is compressed to 200 psig, and- admitted into a evacuated polymerization reaction bomb, charged with highly purified water, and containing 10 ppm ammonium peroxydisulfate and 20 ppm of ammonium perfluorooctanoate, subjected to vigorous shaking, at 60° C. 1.75 g of granular polytetrafluoroethylen resulted. 2.7 g of NaCl was crytallized from the N,N-Dimethylformamide solvent. 4.47 g of dichlorodifluoromethane was reclaimed.

Summary, Ramifications, and Scope

Thus it is now possible to reduce the damage to the stratospheric ozone layer by permanently disposing of dichlorodifluoromethane. Instead of the expense of incineration, it is now possible to convert this environmentally disastrous substance into a plastic of enormous value. Thus the forces of economics will enhance the quality of life on earth by allowing the disposal of a toxic waste to be profitable. By recycling the salts produced, the solvent used, and the mercury, the environmental impact of this process is greatly reduced.

While my description above states many specificities, these should not be construed as limiting the invention's scope. Many variations are possible, such as purification stages between each of the particular processes involved in this waste treatment process. Accordingly, the scope of the invention should be determined not by the embodiment of the drawing, but by the appended claims and their legal equivalents.

I claim:

1. A waste treatment process for the disposal of dichlorodifluoromethane, whereby reducing stratospheric ozone depletion, comprising:

a. electrolyzing an alkaline earth or alklai metal halide salt in an aqueous solution, or anolyte produced by brine saturation, in a cell employing a flowing mercury cathode, whereby producing an alkaline earth or alkali metal amalgam and chlorine, and recycling the anolyte to the brine saturation, and b. adding said alkaline earth or alkali metal amalgam, with alkaline earth or alkali metal concentration in said amalgam between 0.01% and 1%, to a solution of dichlorodifluoromethane in a polar, aprotic solvent, resistant to the reducing action of said alkaline earth or alkali metal amalgam, selected from the group consisting of hydrocarbons, acyclic substituted amides, saturated nitriles, unsubstituted or substituted lactams, sulfones, sulfoxides, ethers, phosphoric esters, and alkyl carbonates; this dechlorination and dimerization reaction is carried out at a temperature varying between −40 and 110 degrees Celsius, at a pressure between one atmosphere and forty atmospheres, evolving tetrafluoroethylene and unreacted dichlorodifluoromethane gases, said reaction being exothermic, and c. recovering alkaline earth or alkali metal chloride salt produced by said reaction from said polar, aprotic solvent by evaporation and crystallization, and d. preparing brine by dissolving said chloride salt in water, and e. using said brine in said mercury cathode cell, producing said alkaline earth or alkali metal amalgam, and f. condensing and recycling said polar, aprotic solvent to said dechlorintion and dimerization reaction, and g. removing spent mercury from said dechlorination and dimerization reaction and reusing in said mercury cathode cell, and h. polymerizing said tetrafluoroethylene gas in an aqueous media, under pressure up to a thousand atmospheres, and temperature up to 350 degrees Celsius, producing tetrafluoroethylene.

2. The process of claim 1 includes said polar aprotic solvent in said dechlorination and dimerization reaction including a promoting agent constituted of salts of the onium type, or of lithium chloride, not reduced by said alkaline earth or alkali metal amalgam in the reaction conditions; the formula of said promoting agent is:

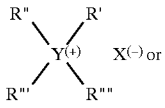 or 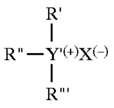

in which Y is nitrogen or phosphorus, and Y' is oxygen or sulfur, and R', R", R'", and R"" are alkyl, aryl, arylalkyl, alkylaryl, or cycloalkyl radicals containing one or more nitrogen, oxygen, or sulfur atoms; X is a halogen anion, or a sulfate group, or cyanooxide group, or an anion of a carboxylic acid, or an analogue of a nonreducible acid; said promoting agent quantity varies between 0.001 and 20 parts by weight to 100 parts by weight of solvent.

3. The process of claim 1 includes introducing an amalgam into a reaction vessel at a rate controlling the temperature, and controlling temperature by cooling.

4. The process of claim 1 includes a polymerization inhibitor selected from a group consisting of terpenes, phenols, quinones, hydrocarbon thiols, ethylenically unsaturated hydrocarbons, aminohydrocarbons, alpha substituted methylvinylbenzenes, and alpha substituted methylvinylmethylbenzenes.

* * * * *